United States Patent [19]

Yokoyama et al.

[11] Patent Number: 5,449,513
[45] Date of Patent: Sep. 12, 1995

[54] PHYSICAL TRAPPING TYPE POLYMERIC MICELLE DRUG PREPARATION

[75] Inventors: Masayuki Yokoyama, Matsudo; Yasuhisa Sakurai, Tokyo; Teruo Okano, Ichikawa; Kazunori Kataoka, Kashiwa, all of Japan

[73] Assignee: Research Development Corporation of Japan, Japan

[21] Appl. No.: 105,535

[22] Filed: Aug. 11, 1993

[30] Foreign Application Priority Data

Aug. 14, 1992 [JP] Japan .................. 4-217044
Aug. 3, 1993 [JP] Japan .................. 5-192586

[51] Int. Cl.6 .................. A61K 9/127; A61K 31/74
[52] U.S. Cl. .................. 424/78.08; 424/78.17; 424/450; 424/451; 424/489; 424/501
[58] Field of Search .................. 424/78.08, 78.17, 450, 424/451, 489, 501

[56] References Cited

U.S. PATENT DOCUMENTS

| | | | |
|---|---|---|---|
| 5,124,151 | 6/1992 | Viegas et al. | 424/422 |
| 5,143,731 | 9/1992 | Viegas et al. | 424/434 |
| 5,161,141 | 6/1992 | Henry | 424/431 |
| 5,219,564 | 6/1993 | Zalipsky et al. | 424/78.17 |

FOREIGN PATENT DOCUMENTS 397307 11/1990 European Pat. Off. .

OTHER PUBLICATIONS

The Merck Index, Eleventh Ed., 1989, pp. 540–541 and 786–787.

*Primary Examiner*—Nathan M. Nutter
*Attorney, Agent, or Firm*—Pennie & Edmonds

[57] ABSTRACT

The present invention relates to drug carriers composed of a block copolymer having hydrophilic and hydrophobic segments, a polymeric micelle type drug comprising hydrophobic drugs trapped by physical treatments in said drug carrier and methods for trapping hydrophobic drugs in the drug carrier. The drugs carrier composed of the block copolymer according to the invention forms a stable polymeric micelle structure with which hydrophobic drugs can be incorporated very efficiently via physical trapping. It was found that the incorporated drug is stably maintained in micelles even in the presence of serum. In addition, a drug difficult to administer into the living body owing to sparing water-solubility for its high hydrophobicity can be administered in the form of polymeric micelle drug.

5 Claims, 6 Drawing Sheets

0    4.28

Elution Volume (ml)

0    4.25

Elution Volume (ml)

PHYSICAL TRAPPING TYPE POLYMERIC MICELLE DRUG PREPARATION

FIELD OF THE INVENTION

The present invention relates to drug carriers having hydrophilic and hydrophobic segments capable of physically trapping hydrophobic drugs, as well as to a polymeric micelle type drug having hydrophilic drugs physically trapped to said carrier.

BACKGROUND OF THE INVENTION

A polymeric micelle type drug, in which a hydrophobic drug is chemically bound to a block copolymer through a covalent bond, was successfully constructed and applied by the present inventors for a patent in Japanese Patent Application No. 116,082/89. In spite of the fact that this prior polymeric micelle type drug is extremely superior as the means of administrating a hydrophobic drug, the combination of hydrophobic drug and block copolymer is disadvantageously limited because its preparation requires functional groups for chemically binding a hydrophobic drug to a block copolymer.

Under the circumstances, however, no development has been made in a method of physically trapping hydrophobic drugs so as to incorporate them in the inner core of polymeric micelle or in a drug carrier for such a method.

The present inventors have tried to develop a physical trapping type polymeric micelle drug, in order to solve the above disadvantage of the chemical bond type polymeric micelle drug. The present inventors, as a result of their eager research, succeeded in preparing a polymeric micelle type drug applicable to a wide variety of combinations of hydrophobic drugs and block copolymer by constructing a polymeric micelle from a drug carrier composed of a block copolymer having hydrophilic and hydrophobic segments and then permitting hydrophobic drugs to be physically trapped into the hydrophobic inner core of said micelle. The system for trapping drugs, developed by the present inventors, allows a wide variety of hydrophobic drugs to be easily incorporated in the polymeric micelle.

SUMMARY OF THE INVENTION

The present invention comprises:
1. A polymeric micelle type drug, which comprises a hydrophobic drugs physically trapped in a drug carrier composed of a block copolymer represented by formula I or II:

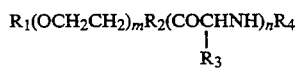

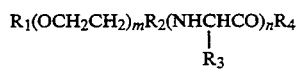

wherein $R_1$ stand for H or an alkyl group, $R_2$ stands for NH, CO, $R_6(CH_2)_qR_7$ (in which $R_6$ represents OCO, OCONH, NHCO, NHCOO, NHCONH, CONH or COO, $R_7$ represents NH or CO, and q represents 1–6), $R_3$ stands for H, an alkyl group, $CH_2C_6H_5$, $(CH_2)_pCOOR_5$ or $(CH_2)_pCONHR_5$ (in which p represents 1 or 2, $R_5$ represents a $C_1$–$C_{20}$ alkyl group, a benzylsubstituted $C_1$–$C_{20}$ alkyl group or a benzyl group), $R_4$ stands for H, OH or a $C_1$–$C_{20}$ alkyl group carrying CO, NH or O in the terminal, m stands for 4–2500, and n stands for 2–300.

2. The drug according to 1, in which the block copolymer is a compound represented by formula III:

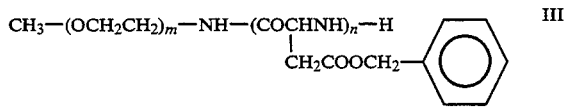

wherein m stands for 4–2500 and n stands for 2–300.

3. The drug according to 1, in which the hydrophobic drug is adriamycin or indomethacin.
4. The drug according to 1, in which the hydrophobic drug is adriamycin, and the block copolymer is a compound of formula III.
5. The drug according to 1, in which the hydrophobic drug is indomethacin, and the block copolymer is a compound of formula III.
6. A method for trapping hydrophobic drugs in drug carrier, which comprises heating, ultrasonication or organic solvent treatment of hydrophobic drugs and drug carrier of formula I, II or III to physically trap said hydrophobic drugs in polymeric micelles composed of said drug carrier.

DETAILED DESCRIPTION OF THE INVENTION

Figure 1:
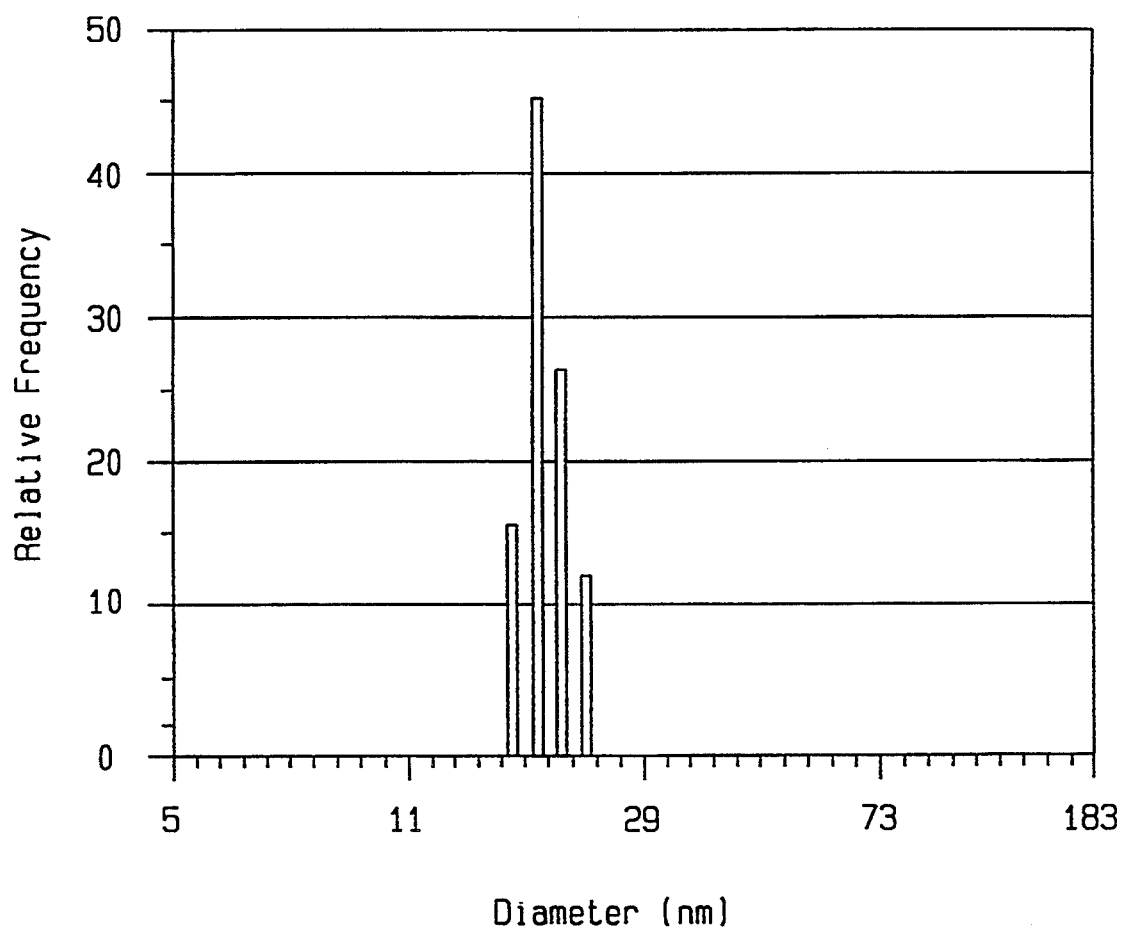
FIG. 1 shows particle size distribution of block copolymer micelles (A-5-10) by dynamic light scattering of polymeric micelles of polyethylene oxide-poly-($\beta$-benzyl L-aspartate) block copolymer (A-5-10) in an aqueous solution.

The hydrophilic segment according to the invention includes e.g. polyethylene oxide, polymalic acid, polyaspartic acid, polyglutamic acid, polylysine, polysaccharide, polyacrylamide, polyacrylic acid, polymethacrylamide, polymethacrylic acid, polyvinyl pyrrolidone, polyvinyl alcohol, polymethacrylate, polyacrylate, polyamino acids and segments derived from derivatives thereof.

The hydrophobic segment according to the invention includes e.g. poly(β-benzyl L-aspartate), poly(γ-benzyl L-glutamate), poly(β-substituted aspartate), poly(γ-substituted glutamate), poly(L-leucine), poly(L-valine), poly(L-phenylalanine), hydrophobic polyamino acids, polystyrene, polymethacrylate, polyacrylate, polymethacrylate amide, polyacrylate amide, polyamide, polyester, polyalkylene oxide other than polyethylene oxide and hydrophobic polyolefins.

Examples of the present block copolymer consisting of hydrophilic and hydrophobic segments are polyethylene oxide-polystyrene block copolymer, polyethylene oxide-polybutadiene block copolymer, polyethylene oxide-polyisoprene block copolymer, polyethylene oxide-polypropylene block copolymer, polyethylene oxide-polyethylene Block copolymer, polyethylene oxide-poly(β-benzylaspartate) block copolymer, polyethylene oxide poly(γ-benzylglutamate) block copolymer, polyethylene oxide-poly(alanine) block copolymer, polyethylene oxide-poly(phenylalanine) block copolymer, polyethylene oxidepoly(leucine) block copolymer, polyethylene oxide-poly(isoleucine) block copolymer, polyethylene oxide-poly(valine) block copolymer, polyacrylic acid-polystyrene block copolymer, polyacrylic acid-polybutadiene block copolymer, polyacrylic acid-polyisoprene block copolymer, polyacrylic acid-polypropylene block copolymer, polyacrylic acid-polyethylene block copolymer, polyacrylic acid-poly(β-benzylaspartate) block copolymer, polyacrylic acid-poly(γ-benzylglutamate) block copolymer, polyacrylic acid-poly(alanine)block copolymer, polyacrylic acid-poly(phenylalanine) block copolymer, polyacrylic acid-poly(leucine) block copolymer, polyacrylic acid-poly(isoleucine) block copolymer, polyacrylic acid-poly(valine) block copolymer, polymethacrylic acid-polystyrene block copolymer, polymethacrylic acid-polybutadiene block copolymer, polymethacrylic acid-polyisoprene block copolymer, polymethacrylic acid-polypropylene block copolymer, polymethacrylic acid-polyethylene block copolymer, polymethacrylic acid-poly(β-benzylaspartate) block copolymer, polymethacrylic acid-poly(γ-benzyl glutamate) block copolymer, polymethacrylic acid-poly(alanine)blockcopolymer, polymethacrylicacid-poly(p-henylalanine) block copolymer, polymethacrylic acid-poly(leucine) block copolymer, polymethacrylic acid-poly(isoleucine) block copolymer, polymethacrylic acid-poly(valine) block copolymer, poly(N-vinylpyrrolidone)-polystyrene block copolymer, poly(N-vinylpyrrolidone)-polybutadiene block copolymer, poly(N-vinylpyrrolidone)-polyisoprene block copolymer, poly(N-vinylpyrrolidone)-polypropylene block copolymer, poly(N-vinylpyrrolidone)-polyethylene block copolymer, poly( N-vinylpyrrolidone)-poly(β-benzylaspartate) block copolymer, poly(N-vinylpyrrolidone)-poly(γ-benzylglutamate) block copolymer, poly( N-vinylpyrrolidone)-poly(alanine) block copolymer, poly(N-vinylpyrrolidone)-poly(phenylalanine) block copolymer, poly(N-vinylpyrrolidone)-poly(leucine) block copolymer, poly(N-vinylpyrrolidone)-poly(isoleucine) block copolymer, poly(N-vinylpyrrolidone)-poly(valine) block copolymer, poly(aspartic acid)-polystyrene block copolymer, poly(asparticacid)-polybutadieneblockcopolymer, poly(aspartic acid)-polyisoprene block copolymer, poly(aspartic acid)-polypropylene block copolymer, poly(aspartic acid) polyethylene block copolymer, poly(aspartic acid)-poly(β-benzylaspartate) block copolymer, poly(aspartic acid)-poly(γ-benzylglutamate) block copolymer, poly(aspartic acid)-poly(alanine) block copolymer, poly(aspartic acid)-poly(phenylalanine) block copolymer, poly(aspartic acid)-poly(leucine) block copolymer, poly(aspartic acid)-poly(isoleucine) block copolymer, poly(aspartic acid)-poly(valine) block copolymer, poly(glutamic acid)-polystyrene block copolymer, poly(glutamic acid)-polybutadiene block copolymer, poly(glutamic acid)-polyisoprene block copolymer, poly(glutamicacid)-polypropyleneblockcopolymer, poly(glutamic acid)-polyethylene block copolymer, poly(glutamic acid)-poly(β-benzylaspartate) block copolymer, poly(glutamic acid)-poly(γ-benzylglutamate) block copolymer, poly(glutamic acid)-poly(alanine) block copolymer, poly(glutamic acid)-poly(phenylalanine) block copolymer, poly(glutamic acid)-poly(leucine) block copolymer, poly(glutamic acid)-poly(isoleucine) block copolymer and poly(glutamic acid)-poly(valine) block copolymer.

The drug to be physically trapped in the hydrophobic inner core of polymeric micelle is not particularly limited. Examples are anticancer drugs such as adriamycin, daunomycin, methotrexate, mitomycin C, etc., painkilling and anti-inflammatory drugs such as indomethacin etc., drugs for the central nervous system, drugs for the peripheral nervous system, drugs against allergies, drugs for the circulatory organs, drugs for the respiratory organs, drugs for the digestive organs, hormones as drugs, metabolizing drugs, antibiotics, drugs for use in chemotherapy, etc.

The physical means of trapping hydrophobic drugs in polymeric micelles composed of the present drug carrier includes heating, ultrasonication and organic solvent treatment, which are conducted solely or in combination with one another. Heating is carried out at 30°–100° C. for a period of time from 10 min. to 24 hours. Ultrasonication is carried out in the range of 1–200 W for a period of time from 1 second to 2 hours. The organic solvent used in organic solvent treatment is DMF, DMSO, dioxane, chloroform, n-hexane, toluene, methylene chloride, etc., which is used in the absence of water or after added in an amount of 0.01% (v/v) or more to water.

Hereinafter, the present invention is specifically explained in detail with reference to the actual incorporation of adriamycin as an anticancer drug, indomethacin as a painkilling, anti-inflammatory drug and pyrene as a typical hydrophobic chemical, into an AB type block copolymer composed of a hydrophilic segment derived from a derivative of polyethylene oxide and a hydrophobic segment of poly(β-benzyl L-aspartate).

The compound of formula IV:

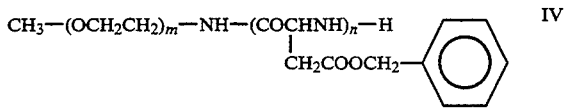

is polyethyleneoxide-poly(β-benzyl-aspartate) block-copolymer consisting of polyethylene oxide and poly(β-benzyl L-aspartate) which have hydrophilic and hydrophobic properties, respectively. The compound of formula III is compound of formula I wherein $R_1$ is a methyl group, $R_2$ is NH, $R_3$ is $CH_2COOCH_2C_6H_5$, and $R_4$ is H.

This block copolymer is prepared by polymerizing, in the presence of an initiator, β-benzyl L-aspartate N-carboxy anhydride from the terminal primary amino group of polyethylene oxide (molecular weight of 200–250,000) having an amino group in one terminal and a methoxy group at the other terminal. The portion of poly(β-benzyl L-aspartate) in the block copolymer polyethylene oxide-poly(β-benzyl L-aspartate) may have a molecular weight varying from 205 to 62,000. By suitable selection of a chain length ratio of the two segments, this block copolymer forms a polymeric micelle with ethylene oxide as an outer shell and poly(β-benzyl L-aspartate) as an inner core. This polymeric micelle can stably incorporate hydrophobic pyrene, adriamycin and indomethacin by heating, ultrasonication, or treatment with organic solvent.

The drug carrier composed of the block copolymer according to the invention forms a stable polymeric micelle structure with which hydrophobic drugs can be incorporated very efficiently via physical trapping into the inner core. A drug difficult to administer into the living body owing to sparing water-solubility for its high hydrophobicity can be administered in the form of polymeric micelle type drug.

In addition, the invention do not require any functional group for chemical bonding and thereby enables a wide variety of combinations of hydrophobic drugs and polymeric micelle.

EXAMPLES

The present invention is described in detail with reference to the following examples, which however are not intended to limit the scope of the invention.

Example 1

β-benzyl L-aspartate N-carboxylic anhydride (1.99 g) was dissolved in 3 ml N,N-dimethylformamide, followed by addition of 15 ml of chloroform. Separately, 4.00 g of polyethylene oxide having methoxy group in one terminal and an amino group in the other terminal (molecular weight: 5,000) was dissolved in 15 ml chloroform, and the solution was then added to the above solution of β-benzyl L-aspartate N-carboxy anhydride. 26 hours thereafter, the reaction mixture was added dropwise to 330 ml diethyl ether, thereby giving rise to polymer precipitates which in turn were recovered by filtration, then washed with diethyl ether and dried under vacuum, to give polyethylene oxide poly(β-benzyl L-aspartate) block copolymer (referred to as "PEO-PBLA," hereinafter) (A-5-10). Yield was 5.13 g (91%). The compositions of block copolymers thus synthesized are summarized in Table 1.

TABLE 1

Characterization of Polyethylene Oxide-Poly(β-Benzyl L-Aspartate) Block Copolymer and Micelles

| Sample | PEO wt (%)[a] | Mn[a] | nPEO | npBLA[a] | Particle size (mm)[b] | CMC (mg/L) |
|---|---|---|---|---|---|---|
| A-5-10 | 73.0 | 7000 | 110 | 9.0 | 18 | 10 |
| A-5-20 | 53.3 | 9100 | 110 | 19 | 17 | 5.0 |
| A-12-20 | 35.0 | 16000 | 270 | 20 | 21 | 10 |

[a] determined by $^1$H-NMR
[b] determined by dynamic light scattering (number-average)

Example 2

Formation of Micelles

The block copolymer synthesized in Example 1 was dissolved at a concentration of 0.01–0.1% (w/v) in water or a suitable buffer. The formation of micelles in the thus obtained solutions was ascertained by measurement of distribution of particle size by dynamic light scattering. The result is set forth in FIG. 1. The particle size of micelle and critical micelle concentration are also shown in Table 1.

Example 3

Incorporation of Pyrene into Micelles

Pyrene of formula V:

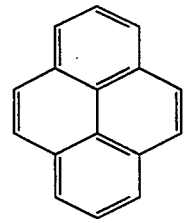

is sparingly soluble in water so that a predetermined amount of pyrene was dissolved at acetone. After dissolved, acetone was removed under a nitrogen atmosphere, and a micelle solution of PEO-PBLA (A-5-10) in distilled water was added at a concentration shown in Table 1 to the pyrene.

1. Incorporation by Stirring

The above mixture was stirred for 2 days so that pyrene was incorporated into micelies.

2. Incorporation by Heating

The above mixture was heated at 80° C. for 2 hours so that pyrene was incorporated into micelies.

3. Incorporation by Ultrasonication

The above mixture was ultrasonicated for 15 seconds so that pyrene was incorporated into micelies.

4. Incorporation by Treatment with DMF for Making the PBLA segment swelled in the PEO-PBLA micelle.

As described above, acetone was removed from the pyrene solution. To the pyrene was added DMF in an amount of 30% relative to the micelle solution to be added afterward. Then, a solution of PEO-PBLA in distilled water was then added in a concentration shown in Table 3 to the pyrene solution. After stirred for 15 hours, the solution was dialyzed in a dialysis tube Spectrapor 6 (cut off molecular weight=1,000) against water. According to the above procedure, pyrene was incorporated into micelles.

Figure 2:
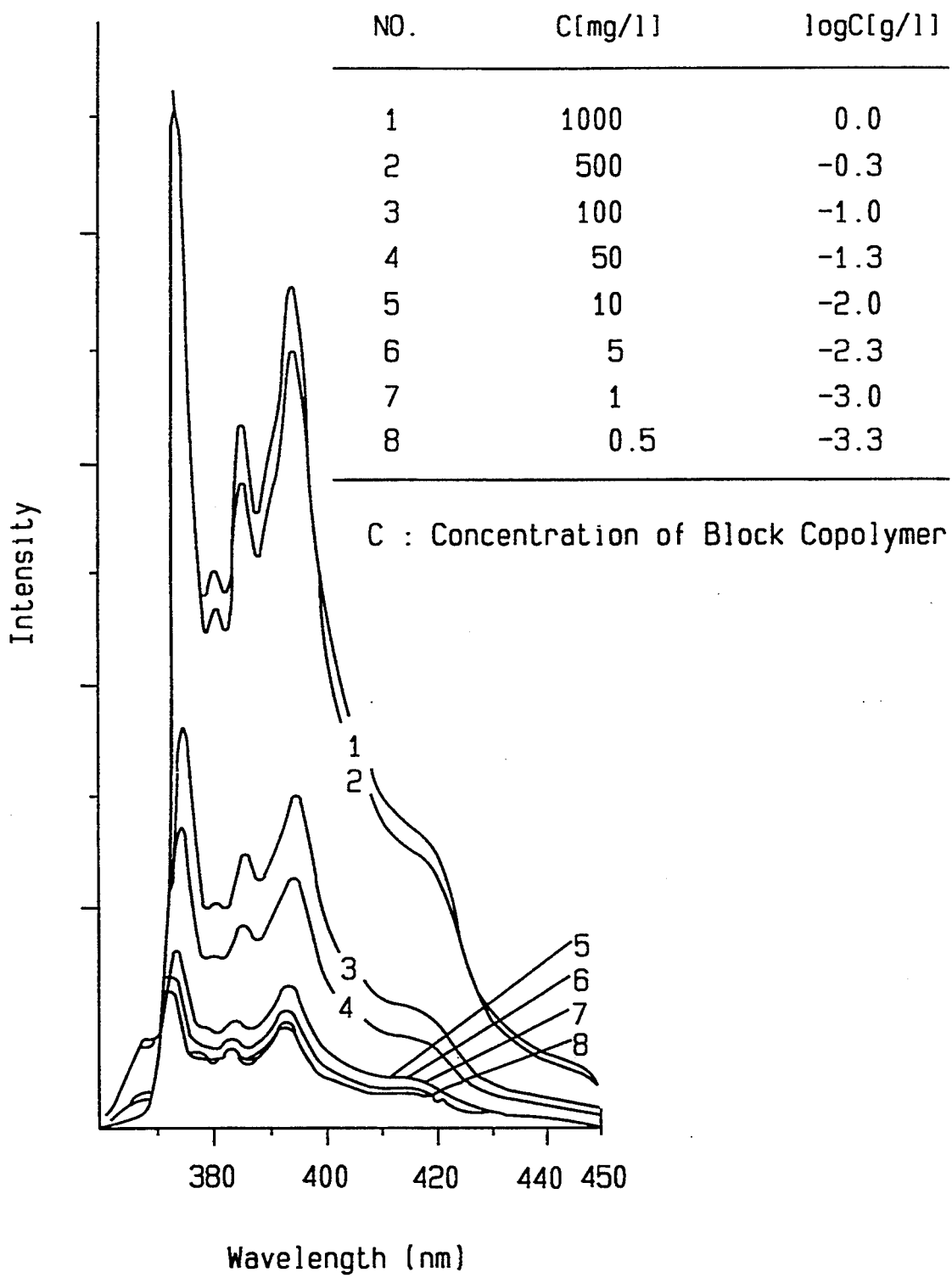
FIG. 2 shows changes in florescence spectra (excitation wavelength: 339 nm) in the presence of aqueous pyrene solution ($6 \times 10^{-7}$M) when incorporated in the inner core of block copolymer micelles (A-5-10) by heating. In the figure, Nos. 1–8 indicate the fluorescence spectra of pyrene at the respective concentrations of block copolymer.
Figure 3:
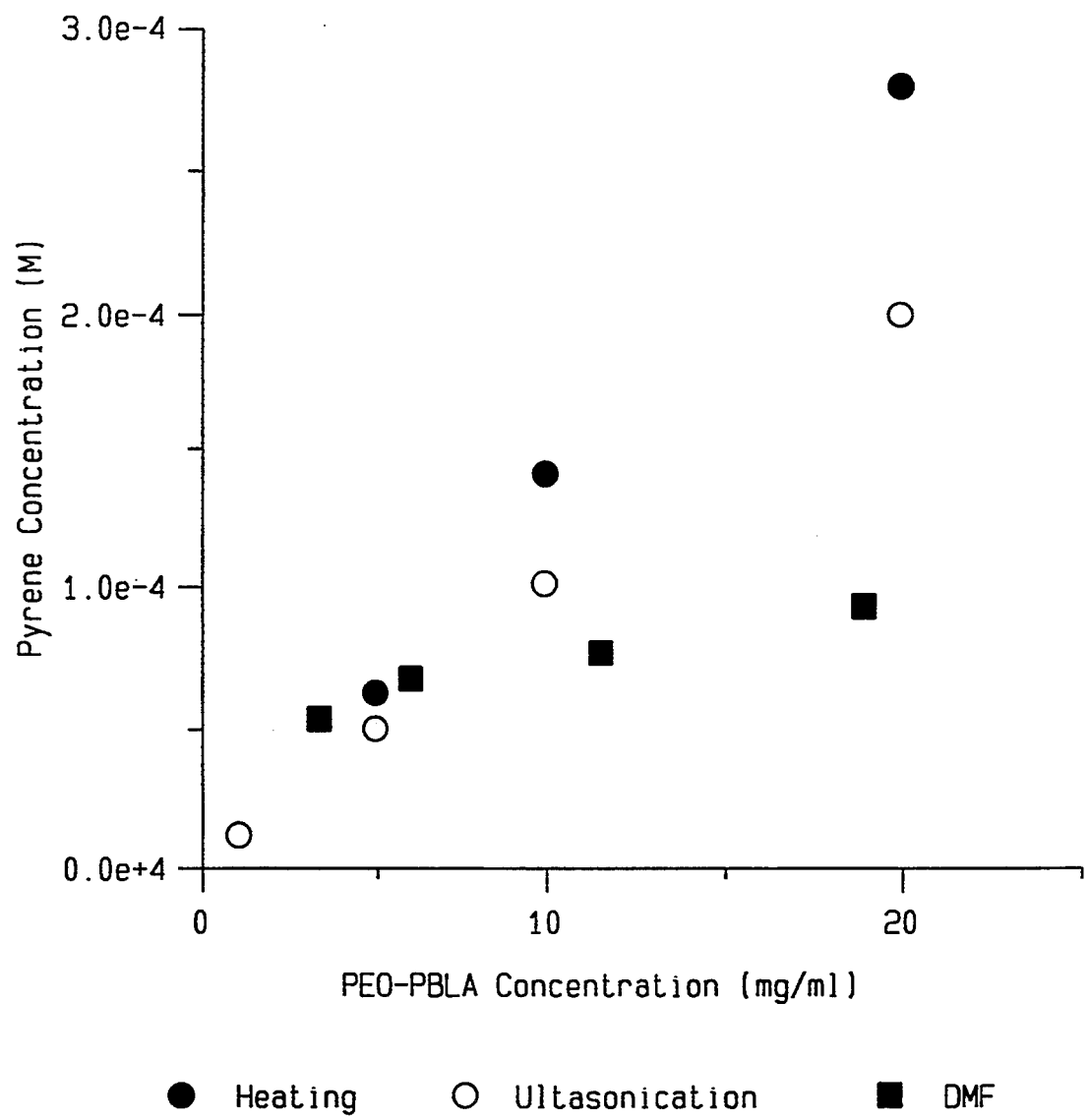
FIG. 3 shows the effect of incorporation means and block copolymer concentration on the amount of pyrene incorporated into block copolymer micelles (A-5-10) by three methods at various concentrations of block copolymer. (●) Heating; (○) Ultrasonification; (■) DMF.

As is evident from increases in the intensities of the fluorescence spectra of the heated sample shown in FIG. 2, the incorporation of pyrene into micelles was confirmed in every incorporation means. FIG. 3 shows a comparison between the amounts of pyrene incorporated into micelles, where the incorporation means by heating attains the amount of incorporated pyrene as approx. 250 times high as the amount of pyrene saturated in water. Table 2 shows the partition coefficient of pyrene into PEO-PBLA (A-5-10) micelle relative to water.

TABLE 2

Distribution Coefficient into Micelle Solution of Polyethylene Oxide-Poly(β-Benzyl L-Aspartate) Block Copolymer

| Means of Incorporating Pyrene | Distribution Coefficient (Kn) |
|---|---|
| Stirring | 17000 |
| Heating at 80° C. | 21000 |
| Ultrasonication | 17000 |

Example 4

5 mg of adriamycin hydrochloride and 5 mg of PEO-PBLA (A-12-20) were added to 5 ml of 0.1M Tris buffer, pH 9.1. Then, adriamycin was made miscible into micelles by stirring and ultrasonication.

Adriamycin is the compound of the following formula:

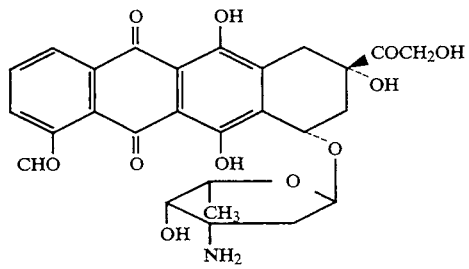

VI

Figure 4:
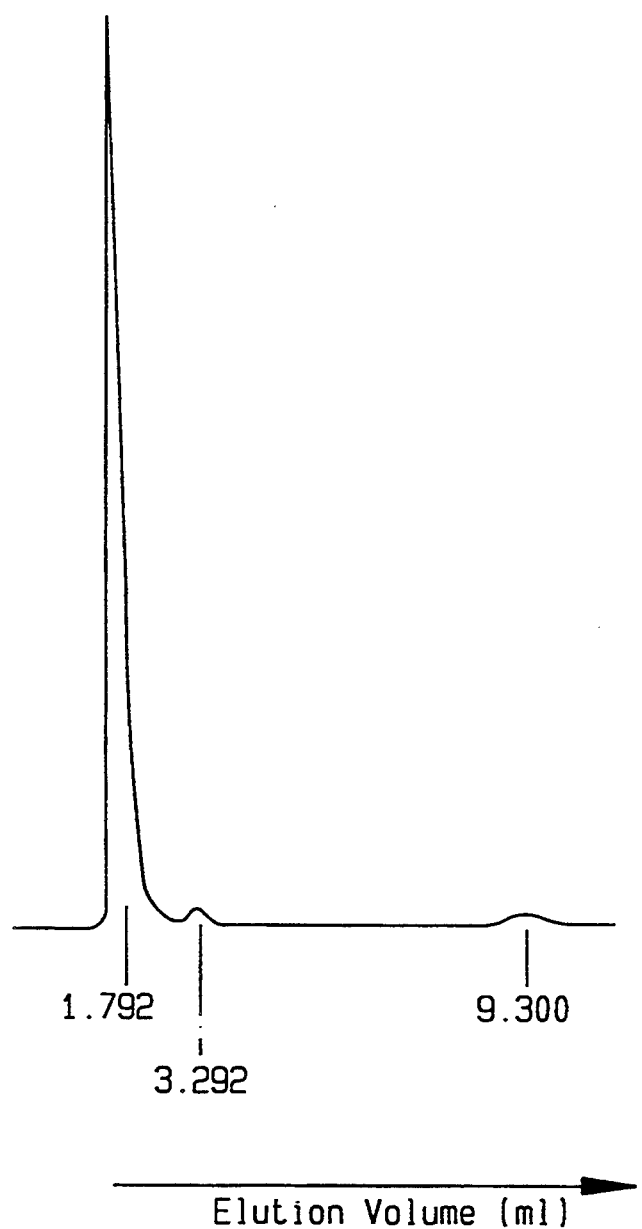
FIG. 4 is a gel permeation chromatogram (GPC) of adriamycin incorporated into polymeric micelles. Column: Asahipak GS-510M; Eluent solvent: 0.1M phosphate buffer, pH 7.4; Flow rate: 1.0 mL/min; Adriamycin Concentration: 10 μg/mL.

This compound itself does not dissolve in Tris buffer, pH 9.1, but can be completely dissolved according to the above procedure. As shown in FIG. 4, adriamycin appeared in gel-exclusion volume in GPC where the sample was monitored at 485 nm at which adriamycin shows characteristic absorption, and this indicates sufficient incorporation of adriamycin into micelles. In FIG. 4, elution volume is indicated as numerical values where 1.792, 3.292 and 9.300 mean micelles, a single polymer and unincorporated adriamycin, respectively.

Example 5

Figure 5:
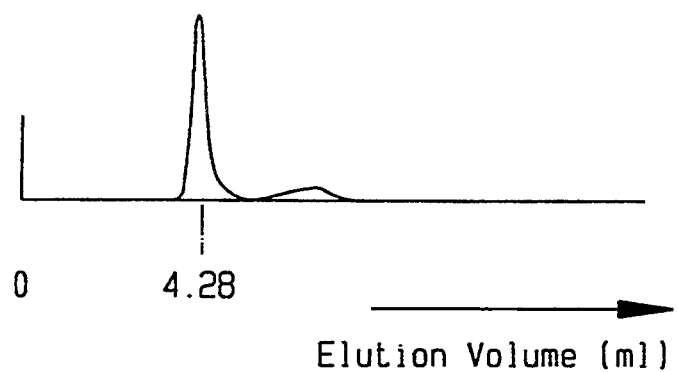
FIG. 5 is a gel permeation chromatogram of polymeric micelles. Column: Asahipak GS-502H; Eluent solvent: 0.1M phosphate buffer, pH 7.4; Flow rate: 1.0 mL/min; Detection 485 nm.
Figure 6:
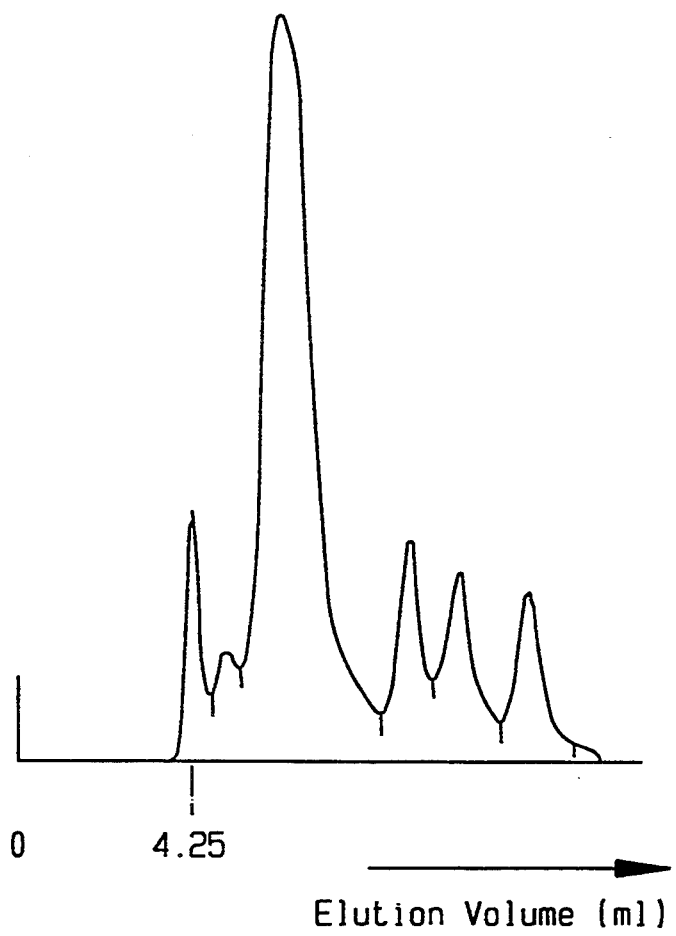
FIG. 6 is a gel permeation chromatogram of adriamycin incorporated in micelles after allowed to stand for 5 hours in the presence of 50% (V/V) of fetal bovine serum. Column: Asahipak GS-520H; Eluent solvent: 0.1M phosphate buffer, pH 7.4; Flow rate: 1.0 mL/min; Detection 485 nm.
Figure 7:
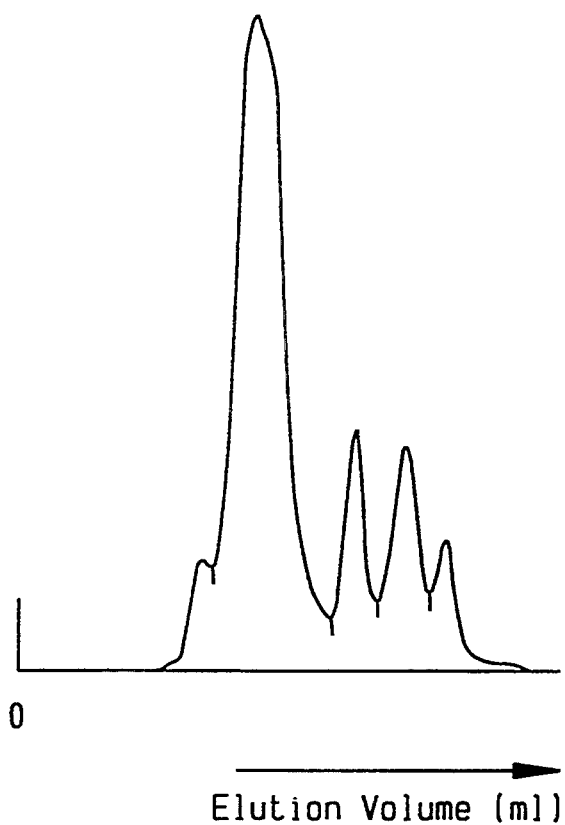
FIG. 7 is a gel permeation chromatogram of 50% (V/V) fetal bovine serum. Column: Asahipak GS-520H; Eluent solvent: 0.1M phosphate buffer, pH 7.4, Flow rate: 1.0 mL/min; Detection: 485 nm.

4.4 μl triethylamine and 20 mg PEO-PBLA block copolymer (A-12-20) were added to a solution of 14 mg adriamycin hydrochloride in 4 ml DMF, and the mixture was stirred for 10 min. and then dialyzed for 15 hours against distilled water. Dynamic light scattering indicated that the sample thus obtained formed polymeric micelles with a weight-average diameter of 55 nm. FIG. 5 shows a gel permeation chromatogram of the polymeric micelles monitored at 485 nm. Adriamycin was incorporated in the micelles, as can be seen from its elution as micelles in gel exclusion volume (4.2–4.3 ml). FIG. 6 shows a gel permeation chromatogram of adriamycin incorporated in micelles after allowed to stand for 5 hours in the presence of 50% (V/V) fetal bovine serum. In FIG. 6, the peak (4.25 ml) eluted in gel exclusion volume and not present in the serum itself was not lowered in the presence of serum (FIG. 7), which indicates that adriamycin can be stably maintained in micells even in the presence of serum.

Example 6

15 mg of indomethacin of formula

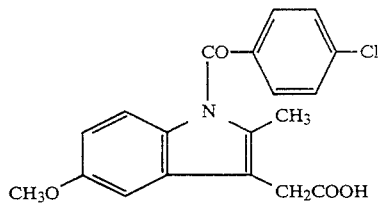

Figure 8:
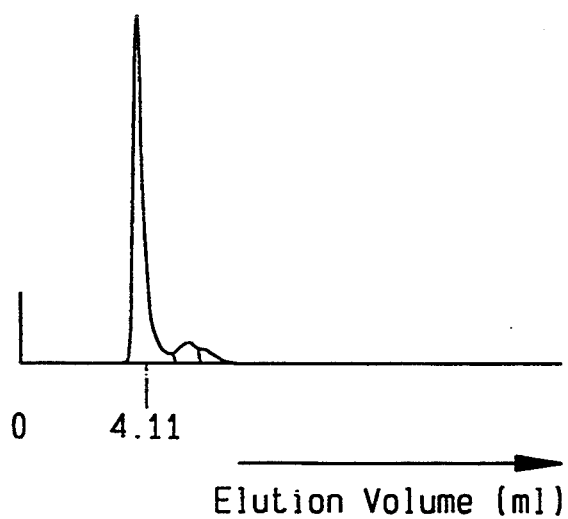
FIG. 8 is a gel permeation chromatogram monitored at 312 nm at which indomethacin shows characteristic absorption. Column: Asahipak GS-520H; Elunet solvent: 1.0M phosphate buffer, pH pH 7.4; Flow rate: 1.0 mL/min; Detection: 312 nm.

VII as an anti-inflammatory drug was dissolved in 4 ml DMF, followed by addition of 20 mg of PEO-PBLA block copolymer (A-12-20). The mixture was stirred for 15 hours and dialyzed for 3 hours against 0.1M phosphate buffer, pH 7.4, and then against water for 6 hours. The resulting sample was found to form polymric micelles with a weight-average diameter of 56 nm, as determined by dynamic light scattering. FIG. 8 shows a gel permeation chromatogram monitored at 312 nm at which indomethacin shows characteristic absorption. The indomethacin was eluted as micelles in gel exclusion volume, indicating the incorporation of the indomethacin into micelles. 0.76 mg of indomethacin was found to be incorporated in the micelles from its adsorption monitored at 312 nm in a solvent of DMF/distilled water (7:3).

What is claimed is:

1. A polymeric micelle type pharmaceutical composition, comprising a hydrophobic drug and a drug carrier, said hydrophobic drug physically trapped within and not covalently bonded to said drug carrier, and said drug carrier composed of a block copolymer represented by the formula I or II:

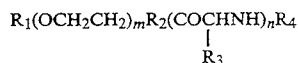

I

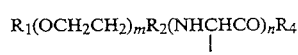

II wherein:

$R_1$ is selected from the group consisting of H and methyl;

$R_2$ is selected from the group consisting of NH, CO and $R_6(CH_2)_qR_7$ where $R_6$ is selected from the group consisting of —OC(O)—, —OC(O)N(H)—, —N(H)C(O)—, —N(H)C(O)O—, —N(H)C(O)N(H)—, —C(O)N(H)— and —C(O)O—;

$R_7$ is NH or CO; and q is 1–6;

$R_3$ is selected from the group consisting of H, —CH$_3$, —CH$_2$CO$_2$H, —CH$_2$CH$_2$CO$_2$H, —CH$_2$CO$_2$CH$_2\phi$, —CH$_2$CH$_2$CO$_2$CH$_2\phi$, —CH$_2$CH(CH$_3$)CH$_3$, —CH(CH$_3$)CH$_2$CH$_3$, —CH(CH$_3$)$_2$, —(CH$_2$)$_p$C$_6$H$_5$, —(CH$_2$)$_p$COOR$_5$ and —CH$_2$C(O)N(H)R$_5$; where p is 1 or 2;

$R_5$ is selected from the group consisting of benzyl and $C_1$–$C_{20}$ alkyl group, said $C_1$–$C_{20}$ alkyl group being optionally substituted with a benzyl group; and $R_4$ is selected from the group consisting of H, —OH, —C(O)-alkyl, —N(H)-alkyl and —O-alkyl, wherein said alkyl is a $C_1$-$C_{20}$ alkyl group;

m=4-2500; and n=2-300.

2. The polymeric micelle type pharmaceutical composition according to claim 1, wherein the block copolymer is a compound represented by the formula III:

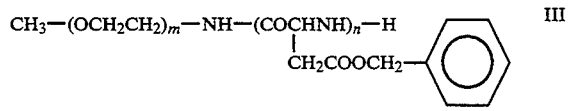
III and wherein m and n are defined as in claim 1.

3. The polymeric micelle type pharmaceutical composition according to claim 1, wherein the hydrophobic drug is selected from the group consisting of adriamycin and indomethacin.

4. The polymeric micelle type pharmaceutical composition according to claim 1 wherein the hydrophobic drug is adriamycin, and the block copolymer is a compound of formula III.

5. The polymeric micelle type pharmaceutical composition according to claim 1, wherein the hydrophobic drug is indomethacin, and the block copolymer is a compound of formula III.

* * * * *